United States Patent [19]

Deneke et al.

[11] 4,152,116

[45] May 1, 1979

[54] COMPOSITION AND METHOD FOR THE DETERMINATION OF ASCORBIC ACID

[75] Inventors: Ulfert Deneke, Peissenberg; Gerhard Michal; Klaus Beauchamp, both of Tutzing, all of Fed. Rep. of Germany

[73] Assignee: Boehringer Mannheim GmbH, Mannheim-Waldhof, Fed. Rep. of Germany

[21] Appl. No.: 920,034

[22] Filed: Jun. 28, 1978

[30] Foreign Application Priority Data

Dec. 9, 1977 [DE] Fed. Rep. of Germany ....... 2754944

[51] Int. Cl.$^2$ .................. G01N 21/06; G01N 31/14; G01N 33/16
[52] U.S. Cl. ................. 23/230 R; 23/230 B; 23/904; 195/103.5 R; 252/408; 422/57
[58] Field of Search ........... 23/230 R, 230 B, 253 TP, 23/904; 252/408; 195/103.5 R

[56] References Cited

U.S. PATENT DOCUMENTS 3,771,964   11/1973   Fader ............................... 23/253 TP
4,056,485   11/1977   Adolf ....................... 195/103.5 R X

OTHER PUBLICATIONS

Chemical Abstracts, 77: 137049g (1972).
Chemical Abstracts, 82: 70120f (1975).

*Primary Examiner*—Sidney Marantz
*Attorney, Agent, or Firm*—Sprung, Felfe, Horn, Lynch & Kramer

[57] ABSTRACT

Ascorbic acid or dehydroascorbic acid is determined by reaction with a tetrazolium salt selected from 3-(4,5-dimethyl-thiazolyl-2)-2,5-diphenyl-tetrazolium bromide, nitrotetrazolium blue, tetrazolium blue chloride and distyryl-nitro blue tetrazolium chloride, in the presence of phenazine methosulphate and a detergent, at a weakly acidic pH value, and evaluating the coloration obtained as a measure of the initial acid content. The method is particularly efficacious in substantially eliminating disturbance of the reaction by foreign substances.

20 Claims, No Drawings

COMPOSITION AND METHOD FOR THE DETERMINATION OF ASCORBIC ACID

The present invention is concerned with a method for the determination of ascorbic acid or dehydroascorbic acid and with a reagent for such determinations.

The determination of ascorbic acid is of great importance, especially in foodstuff chemistry. It is needed for the assessment of the quality of various foodstuffs, for example, fruit juices, fresh vegetables, deep frozen vegetables and the like. Often and particularly in the case of refreshment drinks, a particular vitamin C content is stated which must then also be maintained. However, ascorbic acid is also added as an antioxidant and preservation agent and must then be determined. In the clinical-diagnostic field, the ascorbic acid content of urine is of particular interest since it gives rise to disturbances in the various rapid diagnostics which depend upon redox reactions. The determination of ascorbic acid in the serum is of interest in tropical countries since in such countries avitaminoses (scurvy) are often camouflaged by the symptoms of other diseases to such an extent that they are not diagnosed.

Because of the importance of the determination of ascorbic acid, various methods therefor have already been developed and published; however, their specificity is as a rule, low and their expense, in some cases, considerable. A summary of the known processes, their specificity and their practicability is to be found in Handbuch der Lebensmittelchemie ed. J. Schormüller, Vol. II, 2, pub. Springer-Verlag, Berlin and Heidelberg, 764–789/1967.

The above also applies to dehydroascorbic acid, which is readily formed from ascorbic acid by the action of atmospheric oxygen. Therefore, a sample frequently contains a mixture of ascorbic acid and dehydroascorbic acid. Since dehydroascorbic acid possesses the same vitamin effect as vitamin C, it is usually sensible to determine the dehydroascorbic acid content of a sample.

Processes for the determination of ascorbic acid by means of tetrazolium salts are already known, these reactions proceeding according to the equation:

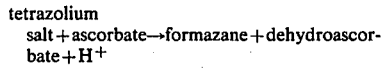
tetrazolium salt + ascorbate → formazane + dehydroascorbate + H$^+$

However, these known processes, which must be carried out in an alkaline medium, are considerably disturbed by numerous substances and were, therefore, only suggested for the determination of pure substances or for pharmaceutical compositions which do not contain comparatively large amounts of disturbing substances. Our own investigations have not confirmed the usefulness of these methods.

The present invention provides a process for the determination of ascorbic acid which does not exhibit or mitigates the above-mentioned disadvantages, is more specific than the known processes and, in particular, does not display the tendency to disturbance by foreign substances which previously occurred in the case of the use of tetrazolium salts. The present process is also applicable to dehydroascorbic acid.

We have now found that, at a weakly acidic pH value, with specific tetrazolium salts and in the presence of a particular electron donor and of a surface-active agent, the disturbance by foreign substances can be practically completely excluded.

Essentially, the process of the present invention, for the determination of ascorbic acid or of dehydroascorbic acid comprises carrying out the above determination reaction in the presence of 3-(4,5-dimethylthiazolyl-2)-2,5-diphenyl-tetrazolium bromide, nitrotetrazolium blue, tetrazolium blue chloride or distyrylnitro blue tetrazolium chloride, together with phenazine methosulfate and a detergent at a weakly acidic pH value, and then evaluating the coloration obtained as a measure of the initial (dehydro)ascorbic acid content.

Amongst the tetrazolium salts which can be used according to the present invention, we have found that 3-(4,5-dimethylthiazolyl-2)-2,5-diphenyl-tetrazolium bromide, in the following referred to as MTT, gives the best results and is, therefore, preferably used according to the present invention.

The tetrazolium salt is preferably used in an amount of 0.01 to 1 mMol/liter of test solution and especially of 0.05 to 0.15 mMol/liter.

As mentioned above, it is important for the process of the present invention to use a weakly acidic pH value. In this pH range, no reaction occurs with most disturbing substances or the reaction is so slowed down that it is of no practical importance. However, at a weakly acidic pH value, the reaction rate with ascorbic acid is too low for a practical determination process. However, due to the presence of phenazine methosulphate, together with a detergent, the reaction of the ascorbic acid is specifically accelerated to such an extent that satisfactory reaction rates are achieved. Surprisingly, however, these additives do not accelerate the reaction with the disturbing substances.

For the adjustment of the weakly acidic pH value, preferably of a pH value of from 4.0 to 6.0 and especially of from 4.8 to 5.3, various buffer systems can be used. These buffer systems, which buffer within the given pH range, are well known. Good reaction rates have been achieved with phosphate buffer, TRA buffer and phosphate/citrate buffer so that these buffers are preferred. The phosphate/citrate buffer gives especially good results since, with this buffer, the proportionality of the extinction change due to the coloured material formed is best fulfilled in the case of all amounts of ascorbic acid. The preferred buffer concentration is from 0.05 to 1 molar, 0.1 to 0.5 mol/liter being especially preferred.

The detergent appropriate in any particular case can easily be ascertained by a few experiments. The highest reaction rates have been achieved with benzalkonium chloride (Zephirol). However, in some samples, this detergent gives rise to the formation of precipitates which can disturb the reaction. The alkylaryl-polyethylene glycol esters have proved to be the best compromise between reaction acceleration and keeping clear of the sample solutions. Other examples of appropriate detergents include polyoxyethylene sorbitan esters, such as sorbimacrogol stearate and polyethylene glycol lauryl ether. Therefore, as a group, the nonionic polyethylene glycol esters and ethers are preferably used according to the present invention, octyl-phenolpolyethylene glycol ester (Triton X100) being especially preferred.

In order to increase the reaction rate, concentrations of detergent of from 0.1 to 1% generally suffice. Above 1%, no further increase of the reaction rate is ascertained. However, since the detergent acts not only as a reaction accelerator but also improves the solubility of the formazane formed, an addition of from 1 to 2% is preferred.

Furthermore, acceleration of the reaction is also brought about by the phenazine methosulphate (PMS) which multiplies the reaction rate and, in particular, brings about a quantitative reaction. This accelerating action was not observed when using other, known electron donors. The concentration of PMS used can be from 0.01 to 1 mMol/liter and, in exceptional cases, can also be higher or lower. A concentration of from 0.05 to 0.15 mMol/liter has proved to be especially useful since, at this concentration, no reaction occurs with SH group-containing compounds, such as homocysteine. SH group-containing compounds can be added when dehydroascorbate present in the test sample is to be simultaneously reduced to ascorbate. This will be dealt with hereinafter.

When the sample to be investigated contains divalent metal ions tending to chelate formation, then chelates can be formed with the coloured formazane material formed which can influence the measurement values. Although chelate formation is admittedly substantially prevented by the preferably used citrate/phosphate buffer, we have found it advisable also to add a small amount of a sequestering agent, for example ethylenediamine-tetraacetic acid or the like, the preferred amounts thereof generally being from 0.1 to 5 mMol/liter. For special purposes, especially in the case of the analysis of samples with a very high content of divalent metal ions, it may, however, be necessary to add larger amounts.

According to a particular embodiment of the process according to the present invention, a parallel test is carried out which contains the same reagent as the determination batch but, in addition, also contains ascorbate oxidase which specifically oxidises the ascorbate contained in the parallel test sample. After termination of this oxidation reaction, this parallel sample is used as blank for the actual ascorbic acid determination. This means that the extinction of the blank is subtracted from the extinction of the actual measurement reaction solution, the difference forming the basis for the calculation of the amount of ascorbic acid.

This preferred embodiment of the process according to the present invention increases still further the specificity of the method, especially when the sample solution contains other substances which react with the tetrazolium salt. The ascorbate oxidase is preferably used in an amount of from 1 to 50 U/ml. of test solution. For routine analyses of particular, substantially uniformly constituted samples, especially of foodstuffs, it can easily be ascertained by a few preliminary experiments which amount of ascorbate oxidase suffices, as a rule, in order quantitatively to oxidise ascorbate present.

As already mentioned above, the process according to the present invention can also be used for the determination of dehydroascorbic acid. For this purpose, the dehydroascorbic acid is first reduced to ascorbic acid and this is then determined in the above-described manner. The reduction is preferably carried out with an organic sulphhydryl compound, homocysteine being preferred. The reducing agent is thereby employed in excess and the reduction is carried out in neutral or weakly alkaline medium. If a sulphhydryl compound is employed, then reduction at a pH value of from 7 to 8 is advantageous. In the case of the preferred homocysteine, the best results are achieved at a pH value of about 7.5. When, subsequently, for the determination of the ascorbic acid formed, a weakly acidic pH value is to be adjusted, the reaction of the ascorbic acid proceeds smoothly, without the excess sulphhydryl compound again reducing the dehydroascorbic acid newly formed in the course of the reaction and thus falsifying the result.

This embodiment of the process according to the present invention can also be employed for the determination of dehydroascorbic acid, besides ascorbic acid. For this purpose, it is merely necessary to determine the ascorbic acid content of a sample in the above-described manner and, in a further sample, first to reduce the dehydroascorbic acid, as described above, and thereafter to carry out the ascorbic acid determination. The amount of dehydroascorbic acid is then given from the difference between the two values.

Under the preferred conditions, the process of the present invention takes place quantitatively in about 30 minutes, i.e. the reaction comes to a stop after about half an hour. The measurement can be carried out, for example, in a commercially available photometer at a wavelength appropriate for the determination of the coloured material formed, such as 578 nm. However, other known methods for the determination of the intensity of a developed coloration can also be used. Evaluation by colour comparison also gives satisfactory results, especially when the process according to the present invention is carried out with the use of a test strip.

The present invention also provides a reagent for the determination of ascorbic acid and dehydroascorbic acid, which comprises 3-(4,5-dimethyl-thiazolyl-2)-2,5-diphenyl-tetrazolium bromide, nitrotetrazolium blue, tetrazolium blue chloride or distyrylnitro blue tetrazolium chloride, as well as phenazine methosulphate, a detergent and a weakly acidic buffer substance, and optionally a sequestering agent for divalent metal ions and/or ascorbate oxidase and/or a sulphhydryl compound.

As buffer, the reagent according to the present invention preferably contains a phosphate/citrate buffer (pH 4.0 to 6). The preferred tetrazolium salt compound is MTT.

A preferred reagent of the above-mentioned kind comprises:
0.01 to 1 mMol/liter of tetrazolium salt,
0.01 to 1 mMol/liter PMS,
0.1 to 2% v/v detergent,
0.1 to 1 mol/liter buffer substance,
1 to 50 U/ml. ascorbate oxidase and
0.1 to 10 mMol/liter sequestering agent, in each case referred to the concentration of the final test solution.

The reagent according to the present invention can be present in a dry or liquid form or as concentrate or as a solution ready for use. All the components, except the ascorbate oxidase, can be present as a mixture.

An especially preferred reagent of the above kind comprises or consists of:
0.05 to 0.15 mMol/liter MTT,
0.05 to 0.15 mMol/liter PMS,
0.5 to 1.5% v/v octyl-phenol polyethylene glycol ester,
0.5 to 5 mMol EDTA, 0.1 to 0.4 mMol/liter phosphate/citrate buffer, pH 4.8 to 5.3 and 1 to 10 U/ml. ascorbate oxidase.

The present invention provides a simple and specific method for the determination of ascorbic acid (vitamin C) and of dehydroascorbic acid which, in comparison with known processes, is substantially more specific and less susceptible to disturbance and can be carried out with simple means. The present invention also provides a reagent for carrying out the process, which reagent can also be in the form of a test strip. In the case of such test strips, an appropriate, preferably planar, carrier material, for example an absorbent paper, such as filter paper or synthetic resin foil, is impregnated with the reagent and then either introduced into the sample to be investigated or the sample is applied thereto dropwise. The evaluation can then take place by colour comparison. The production and construction of test strips are well known and do not here require further description.

The following Examples are given for the purpose of illustrating the present invention:

EXAMPLE 1

Phosphate/citrate buffer, surface-active agent, sequestration agent, tetrazolium salt and PMS, as well as water and sample, were introduced into the cuvette of a commerically-available photometer. The reaction was allowed to proceed and the extinction difference measured against air or water. In a parallel blank, ascorbate oxidase was also employed. The same amount of ascorbate oxidase (AAO) was added to the measurement value sample after termination of the reaction in order to compensate for any extinction differences brought about by the ascorbate oxidase itself.

The details of the process, the reagents used and their amounts are given in the following Table:

TABLE

| | blank (ml.) | Sample (ml.) | concentration in the test |
|---|---|---|---|
| Na$_2$HPO$_4$ 0.4 mol/l.; citric acid 0.2 mol/l., pH 5 + 3% Triton × 100 + 2 mMol/l. EDTA | 1.5 | 1.5 | Na$_2$HPO$_4$ 0.2 mol/l.; citric acid 0.2 mol/l. Triton × 100 1.5% EDTA/l mMol/l. |
| water | 1.0 | 1.0 | |
| sample | 0.1 | 0.1 | 1–50 μmol/l = 0.176 – 8.8 mg/l. ascorbate |
| AAO 500 U/ml. | 0.02 | — | 3.3 U/ml. test solution |

2 min. incubation, then

| MTT 1.5 mMol/l. | 0.2 | 0.2 | 0.1 mMol/l. |
| PMS 1.5 mMol/l. | 0.2 | 0.2 | 0.1 mMol/l. | incubate until the reaction comes to a stop (about 30 min.)

| AAO 500 U/l. | — | 0.02 | 3.3 U/l. |

The above-given composition can be used for the determination of 5 to 250 mg. ascorbate per liter of liquid. In the case of higher concentrations, the sample should be correspondingly diluted and in the case of lower concentrations, the amount of sample can be increased, the water content then being correspondingly lowered.

EXAMPLE 2

Ascorbate determination in orange juice 0.1 ml. of a commercially available orange juice was used directly as sample in the manner described in Example 1, 305 mg. vitamin C/liter being found, which corresponds to the declaration for 4 pounds (2 kg.) of ripe oranges (300 mg./l.). Added ascorbic acid was found 100%. Creep reactions did not occur and the slight turbidity of the orange juice did not influence the determination.

EXAMPLE 3

2.0 g. of a lemon tea drink (Nestea) were dissolved in 20 ml. water and 0.1 ml. of this solution was used in the test according to Example 1. 96 mg. Vitamin C/100 g. dry mass were found. Creep reactions were not observed. Ascorbic acid added to the sample before dissolving was found 99.2%. The slight turbidity of the solution did not influence the test.

EXAMPLE 4

Determination in hips 5 ml. of hip concentrate were dissolved in 100 ml. water. After centrifuging, 0.1 ml. thereof was used in the test according to Example 1. 1770 mg. vitamin C/liter concentrate were found. A slight creep which occurred in the sample and blank was taken into account by extrapolation. Ascorbic acid added before the dilution was found 100.9%. The slight coloration of the diluted extract did not disturb the determination.

EXAMPLE 5

Determination in blackcurrants 1 ml. Blackcurrant juice was diluted with water to 10 ml. and 0.1 ml. thereof employed in the test according to Example 1. 305 mg. vitamin C/liter were found. Ascorbic acid added before the dilution was found 100%. Creep reactions were not observed. In order to test whether the undiluted, strongly coloured juice gave rise to disturbances, it was stored in an open vessel for 4 weeks in a refrigerator in order to lower the ascorbate content. 0.1 ml. of juice was then employed undiluted in the test. 93 mg. vitamin C/liter were still found. The strong sample coloration did not have a disturbing effect. Creep reactions also did not occur. Added ascorbic acid was found completely.

EXAMPLE 6

Determination in beer

Beer which is brewed outside of Bavaria can contain ascorbic acid as a preservative and storage stabiliser. However, the addition of ascorbic acid to beer is forbidden in Bavaria. When carrying out the process of Example 1 on Bavarian beer, no ascorbic acid was found in pale or dark barrel beer or in canned beer. Disturbances were not observed and added ascorbic acid was found completely.

EXAMPLE 7

Determination in spinach

Blanched, deep-frozen spinach was thawed out and thoroughly mixed. 50 g. thereof were worked up by the process of Marchesini et al. (J. Food Science, 39, 568–571/1974) except that, instead of metaphosphoric acid (HPO$_3$)$_n$ phosphoric acid was used. When using 0.2 ml. of the extract, adjusted to pH 5, there was found, according to the process of Example 1, 22 mg. ascorbate/100 g. deep-frozen spinach. In the case of a dry weight of 8%, this corresponds to 275 mg. ascorbate/100 g. dry mass and thus to the findings for blanched spinach of various kinds. Ascorbic acid added before the extraction was found 98.8% Creep reactions were not observed.

EXAMPLE 8
Determination in potatoes 50 g. Potatoes were washed, comminuted and worked up in the same way as the spinach in Example 7. The extract was adjusted to pH 5 and made up to 100 ml. After centrifuging, 500 l. were employed in the test. 18.9 mg. ascorbate/kg. potatoes were found, about 150 mg./kg. being the normal value. However, the potatoes used were old, already very wizened and partially germinated. Under these conditions, the vitamin C content drops very considerably and can even disappear completely. For testing, 75 mg. ascorbic acid were added to the potatoes before the extraction and the extraction process carried out. 97% of this internal standard were found. Creep reactions did not occur.

EXAMPLE 9
Determination in serum

The content of ascorbic acid in the serum should normally be from 2 to 15 mg./liter. Therefore, 1 ml. of sample material, deproteinised with trichloroacetic acid, was used in the test. In 6 different sera, there were found 1.5 to 2.64 mg. ascorbate/liter. Creep reactions did not occur. The finding of added ascorbic acid was practically 100% in the case of adding 17.2 mg. ascorbate/liter of serum.

EXAMPLE 10
Determination in urine

The content of ascorbate in urine can reach considerable values. In the case of normal nutrition, the amount excreted in urine is from 10 to 100 mg/liter. In the case of ingesting amounts higher than 100 mg., 60 to 80% of the amount ingested is again found in the urine so that, in the case of ingesting comparatively large amounts of ascorbic acid, which is today very usual, values greater than 100 mg./liter can also be expected. When using 0.1 ml. amounts of fresh urine, 257 mg. ascorbate/liter were found, the finding rate being 98.3%. No creep reactions or other disturbances were observed.

EXAMPLE 11

Such high vitamin C contents in the urine, as were found in Example 10, can completely or partly suppress the colored material formation of conventional test strips for glucose, blood, bilirubin and the like, which depend upon the oxidation of various leuco dyestuffs, or can lead to false results. Whether this danger exists can be ascertained by a test strip. A round piece of filter paper was, for this purpose, thoroughly washed with 0.2 mol disodium hydrogen phosphate/0.1 mol/liter citric acid buffer (pH 5), sucked dry and dried in a vacuum at ambient temperature. Subsequently, the blank mixture of Example 1, but without sample and ascorbate oxidase, was poured over the filter paper lying in a Petri dish and again dried in a vacuum and with the exclusion of light. On to the so prepared filter paper was dropped one drop each of solutions containing 2, 5, 10, 25 and 50 mg. ascorbate/100 ml. Within one minute, blue-violet spots formed, the color intensity of which increased with increasing amount of ascorbate. Water merely gave a pale yellow color.

It will be understood that the specification and examples are illustrative but not limitative of the present invention and that other embodiments within the spirit and scope of the invention will suggest themselves to those skilled in the art.

What is claimed is:

1. Method for the determination of ascorbic acid or of dehydroascorbic acid, which method comprises reacting a sample solution containing such acid with a tetrazolium salt selected from the group consisting of 3-(4,5-dimethyl-thiazolyl-2)-2,5-diphenyl-tetrazolium bromide, nitrotetrazolium blue, tetrazolium blue chloride and distyryl-nitro blue tetrazolium chloride, in the presence of phenazine methosulphate and a detergent, at a weakly acidic pH value, and evaluating the coloration obtained as a measure of the initial acid content.

2. Method as claimed in claim 1 wherein the pH value is adjusted with a phosphate/citrate buffer.

3. Method as claimed in claim 1 wherein said detergent is an alkylaryl-polyethylene glycol ester.

4. Method as claimed in claim 1 wherein the pH is from 4.0 to 6.

5. Method as claimed in claim 1 wherein a sequestering agent is also present.

6. Method as claimed in claim 1 wherein the said measure of the initial acid content is taken by way of an extinction reading.

7. Method as claimed in claim 6 wherein said extinction reading is adjusted by subtracting therefrom a blank extinction value determined for a blank batch of sample solution with ascorbate oxidase added thereto, after completion of the oxidation reaction.

8. Method as claimed in claim 1 wherein dehydroascorbic acid is determined, which method comprises adding an excess of sulfhydryl compound to the sample solution at a pH from 7 to 8, permitting an oxidation reaction to proceed, adjusting the pH value of the reaction mixture to 4.8 to 5.3, and then determining the ascorbic acid content.

9. Method as claimed in claim 8 wherein said sulfhydryl compound is homocysteine.

10. Reagent for the determination of ascorbic acid and of dehydroascorbic acid, comprising a tetrazolium salt selected from the group consisting of 3-(4,5-dimethyl-thiazolyl-2)-2, 5-diphenyl-tetrazolium bromide, nitrotetrazolium blue, tetrazolium blue chloride or distyrylnitro blue tetrazolium chloride, together with phenazine methosulfate, a detergent, and a weakly acidic buffer substance.

11. Reagent as claimed in claim 11 also containing a sulfhydryl compound.

12. Reagent as claimed in claim 10 also containing ascorbate oxidase.

13. Reagent as claimed in claim 10 also containing a sequestering agent.

14. Reagent as claimed in claim 10 wherein said buffer substance is phosphate/citrate buffer of pH 4.0 to 6.

15. Reagent as claimed in claim 10 containing 3-(4,5-dimethyl-thiazolyl-2)-2,5-diphenyltetrazolium bromide as the tetrazolium salt.

16. Reagent as claimed in claim 10 wherein said detergent is an alkylaryl polyethylene glycol ester.

17. Reagent as claimed in claim 10 comprising:
0.01 to 1 mMol of the tetrazolium salt per liter,
0.01 to 1 mMol phenazine methosulphate per liter,
0.1 to 1 mol buffer substance per liter,
0.1 to 2 wt.% detergent, 1 to 50 U per ml. ascorbate oxidase,
0.1 to 10 mMol sequestering agent per liter, based on final test solution.

18. Reagent as claimed in claim 10 essentially consisting of:
 0.05 to 0.15 mMol 3-(4,5-dimethylthiazolyl-2)-2,5-diphenyltetrazolium bromide per liter,
 0.05 to 0.15 mMol phenazine methosulphate per liter,
 0.5 to 1.5% v/v octylphenyl-polyethylene oxide ether,
 0.5 to 5 mMol ethylenediamine-tetraacetic acid per liter,
 0.1 to 0.4 mMol phosphate/citrate buffer, pH 4.8 to 5.3 per liter,
 1 to 10 U per ml. ascorbate oxidase, based on final test solution.

19. Reagent test strip for the determination of ascorbic acid and/or dehydroascorbic acid comprising, impregnated onto a carrier material, a tetrazolium salt selected from the group consisting of 3-(4,5-dimethylthiazolyl-2)-2,5-diphenyl-tetrazolium bromide, nitrotetrazolium blue, tetrazolium blue chloride or distyrylnitro blue tetrazolium chloride, together with phenazine methosulphate, a detergent, a weakly acidic buffer substance and optionally a sulphhydryl compound and/or ascorbate oxidase and/or a sequestering agent.

20. Reagent as claimed in claim 19 also containing at least one of a sulphhydryl compound, ascorbate oxidase and a sequestering agent.

* * * * *